United States Patent [19]

Paulissen

[11] 4,008,603

[45] Feb. 22, 1977

[54] ULTRASONIC METHOD AND APPARATUS FOR MEASURING WALL THICKNESS OF TUBULAR MEMBERS

[75] Inventor: George T. Paulissen, La Porte, Tex.

[73] Assignee: Shell Oil Company, Houston, Tex.

[22] Filed: Dec. 29, 1975

[21] Appl. No.: 645,051

[52] U.S. Cl. .............................................. 73/67.8 S
[51] Int. Cl.² ...................................... G01N 29/04
[58] Field of Search ........... 73/67.8 S, 67.8 R, 151, 73/67.7

[56] References Cited

UNITED STATES PATENTS

| | | | |
|---|---|---|---|
| 3,028,752 | 4/1962 | Bacon | 73/67.8 R |
| 3,093,998 | 6/1963 | Albertson | 73/67.7 X |
| 3,221,544 | 12/1965 | Gunkel | 73/67.8 |

Primary Examiner—Jerry W. Myracle

[57] ABSTRACT

A method and apparatus for measuring the wall thickness of tubular members using pulses of ultrasonic energy and measuring the time interval between the echoes from the two surfaces of the wall. A rotating diagonal reflector in combination with a fixed transducer is used to scan the interior of the member with the time between the echo from the inner and outer surfaces of the wall being used as a measure of the wall thickness. Each of the time measurements is assigned to a particular counter to accumulate all measurements of a particular thickness. This provides a profile of the wall thickness of the tubular member.

5 Claims, 3 Drawing Figures

ULTRASONIC METHOD AND APPARATUS FOR MEASURING WALL THICKNESS OF TUBULAR MEMBERS

BACKGROUND OF THE INVENTION

The present invention relates to a method and apparatus for inspecting tubular members to detect corrosion and thinning and more particularly to a method and apparatus using ultrasonic energy to measure the thickness of the wall of the tubular member. The use of ultrasonic means for detecting anomalies or other types of imperfections in tubular members is well known. There have also been attempts to adopt ultrasonic means for measuring the thickness of the tubular members. While these attempts have been partially successful, they have not displayed the data in a way that allows the operator to detect the presence of corrosion or a thinning of the tubular member. The ability to detect thinning and corrosion of the tubular members is important especially in the case of heat exchangers where possible tube failure could cause serious problems.

BRIEF SUMMARY OF THE INVENTION

The present invention solves the above problems by providing a non-destructive inspection device using an ultrasonic transducer for producing ultrasonic waves that are directed toward the wall of the tubular member by a rotating acoustical mirror having an inclined surface. A transceiver is provided for energizing the ultrasonic transducer to produce the ultrasonic waves and receive the returning echoes. The time interval between the echo from the inner surface of the tubular member and from the outer surface of the tubular member is measured by digital means. The digital measurements are then analyzed to determine which of the measurements fall within selected time periods. The digital measurements that fall within each of the selected time periods are accumulated on a digital display means. This permits the operator to inspect the digital display means to determine the thickness of the various portions of the wall of the tubular member. A serious corrosion or thinning of the tube wall will be indicated by the accumulation of a number of measurements different from the average time measurement.

In addition to accumulating the time measurements in a series of selected time intervals, they can be displayed in the form of a histogram. This will provide the operator with both an easily inspected and permanent record of the measurements.

BRIEF DESCRIPTION OF THE DRAWINGS

The present invention will be more easily understood from the following detailed description when taken in conjunction with the attached drawings in which.

PREFERRED EMBODIMENT

Figure 1:
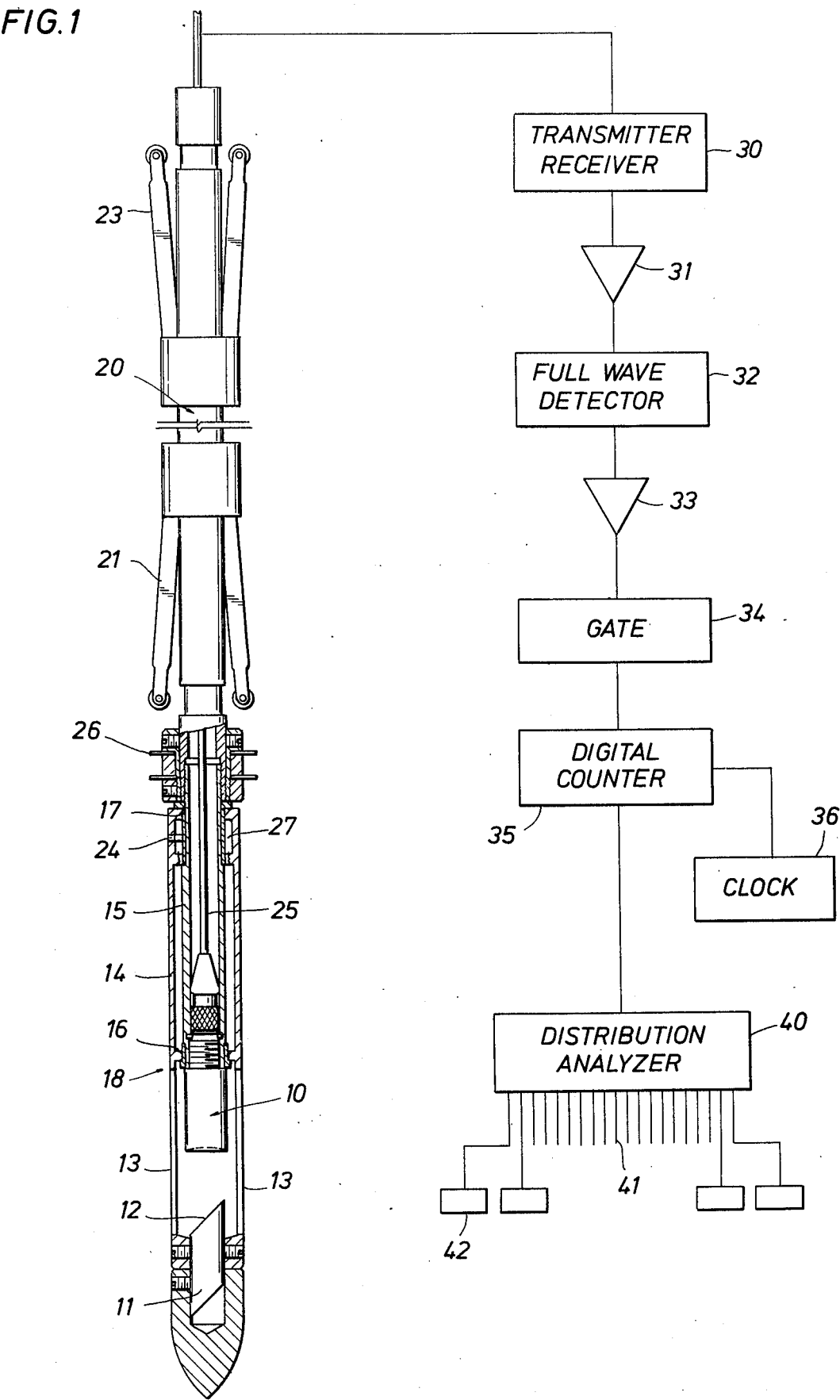
FIG. 1 shows the probe in cross-section while the electronic circuit is shown in block diagram form.

Referring now to FIG. 1, there is shown on the left side a probe that can be inserted in the tubular member to measure the wall thickness. The probe combines an ultrasonic transducer 10 and a rotating mirror 11 having a surface 12 inclined at approximately 45° to the axis of the transducer. The rotating mirror directs the ultrasonic energy normal to the wall of the tubular member and directs the returning echoes to the transducer. The mirror 11 is mounted in one end of a water turbine rotor 14. The turbine rotor is provided with two axially extending arms 13 which support the rotating mirror at the lower end and a series of jet holes 24 that form the turbine at the upper end. The turbine rotor is rotatably supported on the turbine stator 15 by means of two bearings 16 and 17. Provisions are made for introducing water into the cavity 27 surrounding the bearing 17 so that it can flow out the jet holes 24 to spin the rotor 18. The turbine and transducer assembly is supported on the end of a tube 20 which can be a rigid tubular member that is used for inserting the probe into the tubular member being inspected. Centering devices 21 and 23 are provided on the tubular member 20 to center the probe within the tubular member. A flow directing means, for example, two rubber dams 26 are provided on the turbine stator to isolate the lower end of the probe member from the upper end and cause the water which flows out of the jet holes 24 to flow downward. This insures that the tubular member will be filled with water and provide good acoustical coupling between the transducer 10 and the tubular member being inspected. The transducer is coupled to the remainder of the system by a coaxial cable 25 that extends through the tube 20.

The transducer is coupled to a transmitter/receiver 30 which generates a pulse for energizing the transducer and then receives the returning signals. In the present application where the probe is designed for measuring the thickness of the wall of the tubular member, the receiver will receive two or more echoes, one from the inner surface of the wall and one or more from the outer surface of the wall. The transmitter/receiver 30 and the transducer 10 may be commercially available units, for example a model manufactured by Panametrics Incorporated of Waltham, Massachusetts. The signal from the receiver is amplified by an amplifier 31 and supplied to a full wave detector 32. The amplifier 31 should be limited to prevent it from saturating when large amplitude echoes are received. The full wave detector receives the two alternating echo signals from the receiver and converts them to a pair of unidirectional pulses. The full wave detector may comprise a radio frequency transformer, a diode bridge and an integrating circuit. The full wave detector will effectively separate the echoes and produce two distinct signals. The pulses are amplified by an amplifier 33 and used to actuate a gate 34 to produce a single square wave pulse whose leading edge corresponds to the first echo and trailing edge corresponds to the second echo. An additional echo arriving after the first two will be rejected. The pulse from the gate 34 is used to start and stop a digital counter 35 that counts pulses from a clock source 36. Thus, the interval between the first two echoes is converted to a digital time measurement.

At the end of each measurement period, the counter 35 contains a number of counts proportional to the wall thickness discounting the stop/start error. Each display counter memory 42 has a preassigned thickness range which corresponds to a range of counts in the counter 35. The distribution analyzer or gate 40 gates a pulse to increment the counter memory 42 which corresponds to the preassigned block of counts in 35. The number of counts in each counter is displayed in lights for the operator. Each value range corresponds to and is assigned a thickness range for the tube wall material being measured. Thus, by reading the counter an operator may see how often the probe has measured a wall whose thickness was within the thickness range corresponding to that counter. As shown in FIG. 1, the instrument illustrated uses 20 displays representing 20 adjacent thickness value ranges with a 21st counter display being used to accumulate the errors corresponding to those instances in which the transducer failed to receive both returning echoes. A 22nd counter display is used to accumulate the total of the number of measurements.

Figure 2:
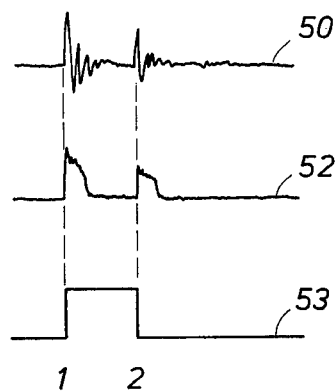
FIG. 2 is a series of waveforms showing the shape of the signal at various positions in the circuitry.

Shown in FIG. 2 are the waveforms which are produced at various portions of the electronic circuit. In particular, waveform 50 illustrates the two echoes that are produced by the receiver and received by the amplifier 31. The signal 52 illustrates the rectified signals with the leading edge of each of the pulses corresponding to the start of the first and second echo, respectively. The waveform 53 corresponds to the pulse produced by the gate circuit 34 which is used to control the operation of the digital counter 35.

Figure 3:
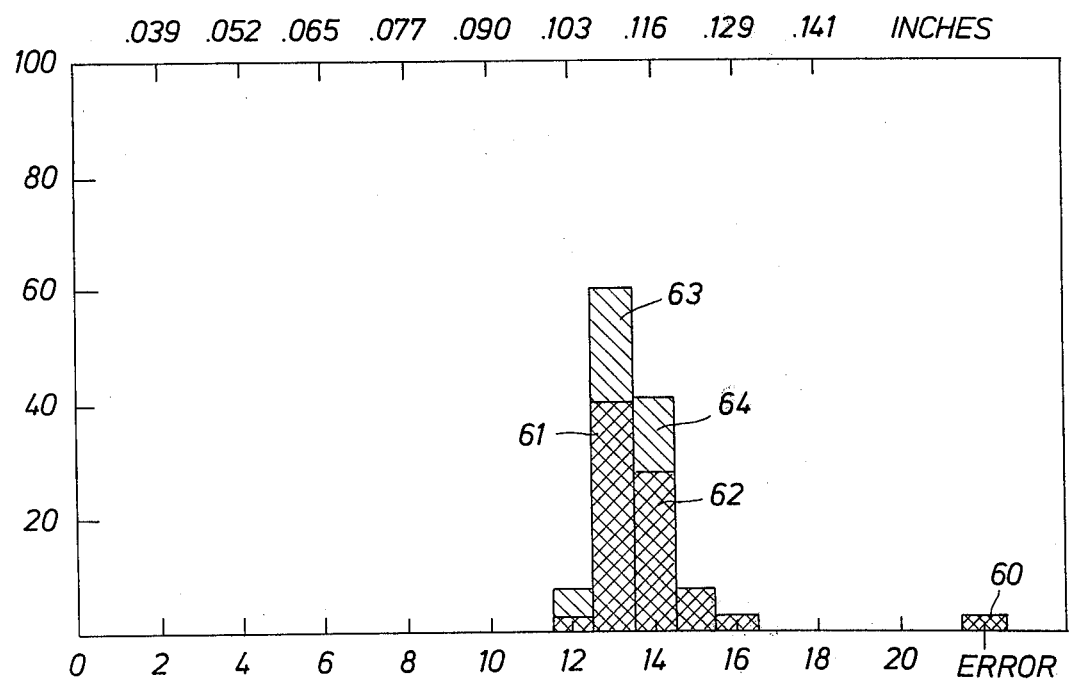
FIG. 3 is a histogram of the measurements made by the instrument compared to those made by the micrometer.

The data accumulated in the various counter memories of the distribution analyzer 40 may be displayed in the form of a histogram as shown in FIG. 3. The twenty channels are shown at the bottom of the graph while the corresponding wall thicknesses are shown at the top. The lefthand edge illustrates the percentage of individual measurements which are accumulated in each of the individual counters. As shown, the error signal 60 corresponds to a small percentage of the total measurements while the majority of the measurements 61 and 62 fall within the two ranges corresponding to the thirteenth and fourteenth counters. The portion of the graphs 63 and 64 appearing above the graphs 61 and 62 illustrate the magnitude of the micrometer measurements made on the same tubular member in which the ultrasonic device is used. While the ultrasonic measurements were spread over a slightly wider range of wall thicknesses than the micrometer range measurements, they did not measure any greatly reduced wall thickness or other abnormalities. Further, from the graph, one would conclude that the average wall thickness of the tubular member was between 0.103 and 0.116 inches.

I claim as my invention:

1. A method for measuring the wall thickness of a tubular member comprising:
    repetitively generating within said member an ultrasonic pulse;
    directing said pulses in a direction normal to the wall of the member;
    detecting the returning echoes of said pulses;
    measuring time period between the echoes from inner and outer walls of the member; and
    accumulating said measured time periods in a series of counter memories, each of said counter memories accumulating the time periods falling within preset limits.

2. The method of claim 1 in which the preset limits of each counter memory corresponds to selected ranges of wall thickness of the member.

3. An apparatus for measuring the wall thickness of a tubular member comprising:
    an ultrasonic transducer;
    a transceiver, said transceiver being coupled to said transducer to energize said transducer to produce an ultrasonic pulse and receive any returning echoes;
    housing means for said transducer, said housing means being adaptable for supporting said transducer within the tubular member to direct a beam of ultrasonic energy along the axis of the tubular member;
    an acoustical mirror, said mirror being rotatably mounted on said housing for rotation about the axis of the tubular member and having a reflecting surface inclined at an angle to said axis to direct the ultrasonic energy towards the wall of the tubular member;
    rotating means, said rotating means being coupled to said mirror;
    a water flow directing means, said water flow directing means being mounted on said housing to produce a water coupling between said transducer, said mirror and the tubular member;
    elapsed time measuring means, said time measuring means being coupled to said transceiver and disposed to measure the time between the echoes from the inner and outer walls of the tubular member; and
    accumulating means, said accumulating means being coupled to said elapsed time measuring means to accumulate the measured times that fall within one of a series of predetermined maximum and minimum time periods.

4. The apparatus of claim 3 in which said accumulating means comprises a plurality of counter memories, one counter memory being assigned to each time period.

5. The apparatus of claim 3 in which said elapsed time measuring means comprises a gate means coupled to said transceiver, said gate means being opened by the receiving of the first echo and closed by the receiving of the second echo to generate a pulse; a clock means for generating a series of clock pulses; a digital counting means, said gate means being coupled to both said clock means and said counting means to supply clock pulses to said counting means for the duration of said gate pulse.

* * * * *